United States Patent
Pullen

(10) Patent No.: US 6,258,369 B1
(45) Date of Patent: Jul. 10, 2001

(54) NON-TOXIC AQUEOUS PESTICIDE

(76) Inventor: Erroll M. Pullen, 11230 N. Scioto Ave., Tuscon, AZ (US) 85737

(*) Notice: Subject to any disclaimer, the term of this patent is extended or adjusted under 35 U.S.C. 154(b) by 0 days.

(21) Appl. No.: 09/282,963

(22) Filed: Mar. 31, 1999

(51) Int. Cl.⁷ .......................... A01N 25/00; A01N 25/34; C07G 17/00; C12N 1/00
(52) U.S. Cl. .......................... 424/405; 424/406; 435/243; 435/267
(58) Field of Search .................................... 424/404, 405, 424/406; 435/243, 267

(56) References Cited

U.S. PATENT DOCUMENTS

| | | | | |
|---|---|---|---|---|
| 5,087,353 | * | 2/1992 | Todd et al. | 210/94 |
| 5,389,257 | * | 2/1995 | Todd et al. | 210/602 |
| 5,753,593 | * | 5/1998 | Pullen et al. | 504/150 |

* cited by examiner

*Primary Examiner*—Deborah K. Ware
(74) *Attorney, Agent, or Firm*—A. W. Fisher, III

(57) ABSTRACT

A non-toxic aqueous pesticide for application on plants and animals comprising at least one surfactant and at least one high terpene containing natural oil. The pesticide is used to effectively control insects and parasites such as lice, ticks, mites, aphides and chiggers found on plants and animals.

8 Claims, No Drawings

NON-TOXIC AQUEOUS PESTICIDE

BACKGROUND OF THE INVENTION

A non-toxic aqueous pesticide to effectively control insects and parasites such as lice, ticks, mites, aphides and chiggers found on animals and plants.

FIELD OF THE INVENTION

Various parasites such as lice, ticks, mites, aphides and chiggers attack untreated and unprotected animals and plants. Poultry are particularly susceptible to parasitic infestations, both internal and external. If left uncontrolled, poultry diseases and parasites can result in reduced productivity and high mortality rates. Thus, effective management and sanitation practices, vaccination and medication are essential to prevent and control diseases and pests.

Only larvae attack poultry or animals. Adult parasites feed on plants. Where poultry is involved, the larvae of these pests attach to the wings and parts of the body injecting a poisonous substance that irritates the skin and causes itching. The larvae feed only for a few days and then drop off. Such infestation is manifest in lesions observable when birds are dressed. This, of course, reduces the value of the poultry. Moreover, the young birds become droopy, refuse to eat and can die.

In the past, various oils have been used to control insects and mites. Recently, however, renewed attention has focused on the use of oils as a natural substitute for traditional insecticides with attendant toxic and other dangerous side effects.

These oils include horticultural oils, which are highly refined petroleum products than can be mixed with water for application for control of target insect and mite pests without deleterious effects. Modern horticultural oils do not include vegetable, fish or whale oils.

Horticultural spray oils are the low toxicity alternative to broad-spectrum insecticides. Since the mechanism of insect and mite control with spray oils is by suffocation and/or repellence of egg laying females, there is no requirement for the addition of toxic chemicals. These properties are a valuable and well recognized component of the practice of integrated pest management where oil spraying is intrinsically linked to natural control of pests by predators and parasitoids. Horticultural spray oils are formulated on highly refined clear oil with a minimum of nonionic surfactant. Independent environmental impact studies have shown that D-C-TRON has no detrimental effect on the environment. Mammalian toxicity studies published in the American Journal of Industrial Medicine have shown that oils at this refinement level are non-toxic and non-carcinogenic.

Aqueous suspensions of malathion, stirofos, Ravap and carbaryl formulations (0.25 to 1.0%) have been tested as dips for control of the northern foul mite (NFM), Ornithonyssus sylviarum (Canestrini and Fanzago) on caged White Leghorn hens. Hens treated with Ravap showed symptoms of organophosphorus insecticide poisoning soon after treatment and some died as a result of the dip. However, dipping with the other insecticides did not result in any apparent toxic effects. Malathion was observed to provide residual control of mites for about 4 weeks post-treatment, but both stirofos and carbaryl dips gave complete control for at least 6 weeks against repeated challenges with the NFM. There were no significant differences in the percent hen-day egg production, feed consumption, or body weight of the hens that could be attributed to any of the chemical treatments.

Generally, oil sprays are safe to humans. These oil sprays have little, if any, negative effect on wildlife and nontarget insects in the environment. Furthermore, oil sprays are less toxic due to the method by which they kill target pests. In particular, the thin film of oil covers the target insect or mite and plugs the spiracles or pores through which the pests or parasites breathe. The cause of death is primarily suffocation. Large, motile insects and animals that breathe by another method are not affected by these oils.

Another advantage of oil applications is the absence of objectionable odors. In addition, oils are relatively inexpensive and significantly less expensive than many insecticides.

Unfortunately, there are limitations to the use of oil treatments. For example, oils are only effective against those pests that are thoroughly coated by the spray solution. This usually means that only small, immobile or slow moving pests that are exposed on the surface of the poultry, animal or plant at the time of application will be controlled.

Since oil sprays only work by contracting and covering the target pest, thorough application is essential. Missed surface areas provide a safe refuge for the target pests. Thus, there remains a need for a non-toxic pesticide that can be effectively applied to the host to control or kill by contacting the target pests.

SUMMARY OF THE INVENTION

The present invention relates to a non-toxic aqueous pesticide for application on plants and animals comprising at least one surfactant and at least one high terpene containing natural oil to effectively control insects and parasites including lice, ticks, mites, aphides and chiggers found on plants and animals.

High terpene containing natural oil as used herein means those natural oils having a terpene content of at least fifty (50%) percent. It is preferable that the high terpene natural oil contains at least ninety (90%) percent. Suitable high terpene containing natural oils includes oil from conifers such as citrus peel oils, preferably orange oil, grapefruit oil, lemon oil or pine oil. Of these, orange oil is the most preferred. Naturally, the amount of high terpene containing natural oils in the non-toxic aqueous pesticide will depend upon the amount of terpenes in the specific oil used.

The surfactant may comprise conventional surfactants such as anionic and nonionic surfactants. Preferred are anionic surfactants such as salts of fatty acids, alkyl sulphates, alkyl ether sulphonates and alkyl aryl sulphonates. Examples of preferred surfactants include sodium dodecylbenzene sulphonate, sodium lauryl ether sulphate and salts such as sodium salts of secondary alkane sulphonates.

Examples of more preferable surfactants include alkyl benzene sulfonic acid, sodium olefin sulfonate, sodium laurel ethoxy sulphate, linear alcohol exthoxylate such as lauryl alcohol ethoxylate, alkane sulphonate and alkyl sulphonic acid.

The non-toxic aqueous pesticide may also contain various additives such as antioxidants, preservatives, pH neutralizers and/or clarifiers.

Since the non-toxic aqueous pesticide is an aqueous composition, the balance of the non-toxic aqueous pesticide is water.

In use, the non-toxic aqueous pesticide is diluted and sprayed or misted on the host, whether plant or animal, to directly contact the surface of the target pests. In some cases, repeated applications may be required.

When so applied, the non-toxic aqueous pesticide is effective in controlling lice, ticks, mites, aphides and chiggers. Since the mechanism of insect and mite control with spray oils is by suffocation and/or repellency of egg laying females, there is no requirement for the addition of toxic chemicals. As such, the instant invention provides a virtually non-toxic alternative to broad spectrum insecticides.

The invention accordingly comprises the features of construction, combination of elements, and arrangement of parts which will be exemplified in the construction hereinafter set forth, and the scope of the invention will be indicated in the claims.

DETAILED DESCRIPTION OF THE PREFERRED EMBODIMENT

The present invention relates to an environmentally compatible non-toxic aqueous pesticide comprising at least one surfactant and at least one high terpene containing natural oil to effectively control target insects and parasites including lice, ticks, mites, aphides and chiggers found on plants and animals.

High terpene containing natural oil as used herein means those natural oils having a terpene content of at least fifty (50%) percent. It is preferable that the high terpene natural oil contains at least ninety (90%) percent. Suitable high terpene containing natural oils includes oil from conifers such as citrus peel oils, preferably orange oil, grapefruit oil, lemon oil, or pine oil. Of these, orange oil is preferred and cold pressed orange oil the most preferred.

Naturally, the amount of high terpene containing natural oils in the non-toxic aqueous pesticide will depend upon the amount of terpenes in the specific oil used. Generally, the non-toxic pesticide composition contains from about 1% to about 15% by weight of high terpene containing natural oil, preferably from about 4% to about 10% by weight and more preferably from about 5% to about 7% by weight.

While not to be bound by theory, it is believed that the terpenes in the natural oils provide a mechanism for the efficacy of the instant invention. In particular, the thin film of oil covers the target insect or mite and plugs the spiracles or pores through which such pests or parasites breathe. Thus the cause of death is primarily suffocation. Large, motile insects and animals that breathe by another method are not affected by these oils. Further, since the high terpene containing oils are natural oils, the non-toxic aqueous pesticide is environmentally acceptable and has little, if any deleterious effect on wildlife and non-target insects.

Surfactants such as anionic and nonionic surfactants are acceptable for use in the non-toxic aqueous pesticide of the present invention. Preferred are anionic surfactants such as salts of fatty acids, alkyl sulphates, alkyl ether sulphonates and alkyl aryl sulphonates. Examples of preferred surfactants include sodium dodecylbenzene sulphonate, sodium lauryl sulphate and salts such as sodium salts of secondary alkane sulphonates.

Examples of more preferable surfactants include alkyl bezene sulfonic acid, sodium olefin sulfonate (40% concentrate), sodium lauryl ethoxy sulphate (60% concentrate), linear alcohol exthoxylate such as lauryl alcohol ethoxylate, alkane sulphonate and or alkyl sulphonic acid.

Generally, the non-toxic aqueous pesticide will contain from about 10% to about 40% by weight of surfactant(s), preferably from about 20% to about 35% by weight and more preferably from about 25% to about 30% by weight.

The non-toxic aqueous pesticide may also contain various additives such as antioxidants, preservatives, pH neutralizers and/or clarifiers.

An example of a suitable antioxidant is butylated hydroxytoluene. The antioxidant added to the non-toxic aqueous pesticide may range of from about 0.01% to about 1% by weight, preferably from about 0.08% to about 0.12% by weight and more preferably about 0.1% by weight.

Examples of suitable preservatives include borax 10 mole. the preservatives may be added to the non-toxic aqueous pesticide in an amount from about 0.1% to about 5% by weight, preferably from about 0.5% to about 2.0% by weight and more preferably about 1.0% by weight.

Caustic crystals such as sodium hydroxide may be added in an amount from about 1.0% to about 1.5% by weight and more preferably about 1.3% by weight to clarify the non-toxic aqueous pesticide.

An example of a suitable pH neutralizer is urea in an amount from about 0.5% to about 1.5% by weight and more preferably about 0.9% by weight.

The non-toxic aqueous pesticide further includes a bactericide such as methyl parapin and propyl parapin in an amount from about 0.5% to about 1.0% by weight and more preferred about 0.7% by weight.

Since the non-toxic aqueous pesticide is an aqueous composition, the balance of the non-toxic aqueous pesticide is from about 60% to about 70% of water by weight.

The preferred non-toxic aqueous pesticide comprises about 6% cold pressed orange oil, about 7% sodium laurel ethoxy sulphate (60% concentrate) or sodium lauryl sulfate, about 9% of linear alcohol ethoxylate, about 1.8% sodium olefin sulfonate (40% concentrate), about 10.6% alkyl benzene sulphonic acid and about 0.7% methyl parapin and propyl parapin with the balance water, all by weight.

In addition, about 0.1% butylate hydroxytoluene antioxidant, about 1.0% borax 10 mole preservative, about 0.9% urea pH neutralizer and about 1.3% sodium hydroxide caustic crystal clarification, all by weight, may be added.

In use, the non-toxic aqueous pesticide is diluted with water and sprayed or misted on the host whether plant or animal to directly contact the surface of the target pests at an effective dilution rate of from about 1:25 to about 1:75 by weight with a preferred dilution rate of from about 1:50 to about 1:60 weight with water. In some cases, repeated applications may be required.

When so applied, the non-toxic aqueous pesticide has been effective in controlling lice, ticks, mites, aphides and chiggers. Since the mechanism of insect and mite control with spray oils is by suffocation and/or repellency of egg laying females, there is no requirement for the addition of toxic chemicals. As such, the instant invention provides a virtually non-toxic alternative as applied to broad spectrum insecticides.

While the invention has been described above with respect to certain particular embodiments thereof, numerous other forms and modifications will be apparent to those skilled in the art. The appended claims and the invention generally should be construed as covering all such obvious forms and modifications which are within the true spirit and scope of the invention.

What is claimed is:

1. A method of controlling insects and parasites found on plants and animals by applying a nontoxic aqueous pesticide to the plant or animal, the pesticide comprising at least one surfactant selected from the group consisting of sodium laurel ethoxy sulphate, alcohol ethoxylate, olefin sulphonate, sulphonic acid and mixtures thereof and at least one high terpene containing natural oil selected from the group consisting of citrus peel oils, pine oils and mixtures thereof, the pesticide containing from about 20% to about 35% by weight percent of said surfactants and from about 4% to about 10% by weight percent of said high terpene containing natural oils, and from about 60% to about 70% of water by weight percent, said pesticide diluted with water at a dilution rate of from about 1:25 to about 1:75 for application to said plant or animal to effectively control lice, ticks, mites, aphids and chiggers.

2. The method of claim 1 wherein the pesticide further includes from about 0.5% to about 1.0% bactericide by weight percent.

3. The method of claim 1 containing from about 25% to about 30% of the surfactants by weight percent and from about 5% to about 7% of high terpene containing natural oils by weight percent.

4. The method of claim 3 containing about 0.7% bactericide by weight percent.

5. The method of claim 4 further containing about 0.1% butylated hydroxytoluene by weight percent, about 1.0% borax 10 mole by weight percent, about 0.9% urea by weight percent and about 1.3% sodium hydroxide by weight percent.

6. A method of controlling insects and parasites found on plants and animals by applying a nontoxic aqueous pesticide to the plant or animal, the pesticide comprising about 6% orange oil by weight percent, about 7% sodium laurel ethoxy sulphate by weight percent, about 9% alcohol ethoxylate by weight percent, about 1.8% sodium olefin sulfonate by weight percent, and about 10.6% alkyl benzene sulphonic acid by weight percent, and from about 60% to about 70% of water by weight percent, said pesticide diluted with water at a dilution rate of from about 1:25 to about 1:75 for application to said plant or animal to effectively control lice, ticks, mites, aphids and chiggers.

7. The method of claim 6 further comprising about 0.1% butylated hydroxytoluene by weight percent about 1.0% borax 10 mole by weight percent, about 0.9% urea by weight percent and about 1.3% sodium hydroxide by weight percent.

8. The method of claim 6 comprising about 0.7% bactericide by weight percent.

\* \* \* \* \*